United States Patent
Malanga et al.

(10) Patent No.: US 11,478,378 B2
(45) Date of Patent: Oct. 25, 2022

(54) SYSTEMS AND METHODS FOR PRESERVATIVE REMOVAL FROM OPHTHALMIC FORMULATIONS

(71) Applicant: TearClear Corp., Copley, OH (US)

(72) Inventors: Michael T. Malanga, Midland, MI (US); Michael Williams, Keystone Heights, FL (US); Srini Venkatesh, Copley, OH (US)

(73) Assignee: TEARCLEAR CORP., Copley, OH (US)

(*) Notice: Subject to any disclaimer, the term of this patent is extended or adjusted under 35 U.S.C. 154(b) by 0 days.

(21) Appl. No.: 17/394,023

(22) Filed: Aug. 4, 2021

(65) Prior Publication Data

US 2022/0039997 A1    Feb. 10, 2022

Related U.S. Application Data

(60) Provisional application No. 63/061,561, filed on Aug. 5, 2020.

(51) Int. Cl.

| *A61F 9/00* | (2006.01) |
| *A61K 31/222* | (2006.01) |
| *A61K 31/498* | (2006.01) |
| *B01J 20/28* | (2006.01) |
| *B01J 20/26* | (2006.01) |
| *A61K 47/18* | (2017.01) |

(52) U.S. Cl.
CPC .......... *A61F 9/0008* (2013.01); *A61K 31/222* (2013.01); *A61K 31/498* (2013.01); *A61K 47/186* (2013.01); *B01J 20/261* (2013.01); *B01J 20/267* (2013.01); *B01J 20/28047* (2013.01)

(58) Field of Classification Search
CPC ....... A61F 9/00; A61F 9/0008; A61K 31/222; A61K 31/498; A61K 47/186; B01J 20/261; B01J 20/26; B01J 20/267; B01J 20/28047
USPC ......................................................... 604/290
See application file for complete search history.

(56) References Cited

U.S. PATENT DOCUMENTS

| 3,293,112 | A | 12/1966 | Kehr |
| 3,322,711 | A | 5/1967 | Bush et al. |
| 4,459,388 | A | 7/1984 | Hettche et al. |
| 5,056,689 | A | 10/1991 | Heyl et al. |
| 5,064,908 | A | 11/1991 | Schuster et al. |
| 5,080,800 | A | 1/1992 | Heyl et al. |
| 5,401,811 | A | 3/1995 | Stuart, Jr. |
| 7,622,031 | B2 | 11/2009 | Seven et al. |
| 10,123,904 | B2 | 11/2018 | Chauhan et al. |
| 11,096,865 | B2* | 8/2021 | Wilson ................. A61K 31/517 |
| 2010/0285192 | A1 | 11/2010 | Daoust et al. |
| 2010/0305259 | A1 | 12/2010 | Rodriguez et al. |
| 2013/0127071 | A1 | 5/2013 | Sugimoto et al. |
| 2017/0224531 | A1 | 8/2017 | Chauhan et al. |
| 2020/0246222 | A1* | 8/2020 | Malanga ............ B01D 39/1676 |
| 2020/0346186 | A1* | 11/2020 | Wilson .................. A61J 1/1456 |

FOREIGN PATENT DOCUMENTS

| CN | 114096339 A | 2/2022 |
| GB | 1087915 A | 10/1967 |
| WO | WO-2005066219 A1 | 7/2005 |
| WO | WO-2016085885 A1 | 6/2016 |
| WO | WO-2018102817 A1 | 6/2018 |
| WO | WO-2019060846 A1 | 3/2019 |
| WO | WO-2019195734 A1 | 10/2019 |
| WO | WO-2020223527 A2 | 11/2020 |
| WO | WO-2022031841 A1 | 2/2022 |

OTHER PUBLICATIONS

Clariant International Ltd. Licolub(R) H 12 fine grain. Oxidized, high density polyethylene max. (2014).
Deurex, The Wax Company. Polyethylene waxes, technical data (2020).
PCT/US2020/030801 International Preliminary Report on Patentability dated Nov. 2, 2021.
PCT/US2020/030801 International Search Report and Written Opinion dated Aug. 4, 2020.
U.S. Appl. No. 16/932,623 First Action Interview dated Jan. 4, 2021.
International Search Report and Written Opinion dated Jan. 19, 2022 for International Application No. PCT/US2021/445334.

* cited by examiner

*Primary Examiner* — Edward M Johnson
(74) *Attorney, Agent, or Firm* — Wilson Sonsini Goodrich & Rosati (57) ABSTRACT

A system comprising a preservative-removing polymeric matrix comprising an active matrix component and an inactive matrix component. A method for administering an ophthalmic agent comprises providing a solution, emulsion, or suspension comprising an ophthalmic agent, and a preservative; and providing a preservative-removing polymeric matrix comprising an active matrix component and an inactive matrix component, and wherein the polymeric matrix is configured to selectively absorb the preservative when the solution, emulsion, or suspension is passed therethrough.

25 Claims, 2 Drawing Sheets

SYSTEMS AND METHODS FOR PRESERVATIVE REMOVAL FROM OPHTHALMIC FORMULATIONS

CROSS-REFERENCE

This application claims the benefit of U.S. Provisional Application No. 63/061,561 filed Aug. 5, 2020, which is incorporated by reference in the disclosure of this application.

FIELD OF INVENTION

The present disclosure generally relates to systems and methods for removal of preservatives and removing a preservative from a fluid comprising a therapeutic agent.

BACKGROUND

Prior approaches to the removal of a preservative from a fluid comprising an ophthalmic agent prior to administration to an eye may be less than ideal in at least some respects. Patients suffering from chronic diseases may use daily eye drop instillations, for example for the treatment of glaucoma. In order to prevent bacterial growth, commercially available eye drop formulations typically use a preservative, in order to address possible bacterial contamination.

The potential for ocular damage from the preservatives may be elevated among patients suffering from chronic diseases which may require daily eye drop instillations for periods of years to decades, such as glaucoma patients. Potential toxic side effects from preservative-free eye drops can be lower than from their preserved counterparts. Patients using preserved eye drops and experiencing toxicity symptoms, such as allergy, blepharitis, or dry eye, may show improvement upon switching to preservative-free formulations.

Although preservative removal devices have been proposed, the prior approaches can be less than ideal and overly complex, in at least some instances. For example, some prior approaches can remove more therapeutic agent than would be ideal, for example, in an effort to produce "preservative-free" eye drops. Other prior approaches may absorb the ophthalmic agent over time resulting in varying dosage as a function time, which may reduce the shelf life of the eye drop formulation.

SUMMARY

The present disclosure relates to systems and methods for removing a preservative from a solution, emulsion, or suspension comprising an ophthalmic agent. In light of the above, there is a clear unmet need for improved systems and methods for removing a preservative from a fluid comprising an ophthalmic agent and a preservative. One technical problem to be solved in meeting this unmet need is the ability to selectively remove the preservative without changing the concentration of the therapeutically effective ophthalmic agent in the fluid. In some cases, the interaction between the ophthalmic agent and a preservative removing device may be tuned by the addition of a support matrix having no affinity for the ophthalmic agent or preservative. Ideally these systems and methods would address at least some of the above drawbacks of prior approaches and reduce patient exposure to preservative while maintaining consistent dosage.

In an aspect, a method for administering an ophthalmic agent is provided. The method may comprise: providing a solution, emulsion, or suspension comprising an ophthalmic agent, and a preservative; and providing a polymeric matrix, wherein the polymeric matrix is configured to selectively absorb the preservative when the solution, emulsion, or suspension is passed therethrough, and wherein the polymeric matrix comprises an active matrix component and an inactive matrix component. The inactive matrix component has substantially no affinity for the ophthalmic agent or the preservative.

In some embodiments, the active polymeric matrix component is a polymeric hydrogel. In some embodiments, the polymeric matrix comprises 2-hydroxyethylmethacrylate. In some embodiments, the polymeric matrix comprises tert-butyl methacrylate. In some embodiments, the polymeric matrix comprises a crosslinker. In some embodiments, the crosslinker is SR-9035.

In some embodiments, the inactive polymeric matrix component is a polyolefin. In some embodiments, the polyolefin is a polyethylene, polypropylene or copolymers thereof. In some embodiments, the polyolefin is a low-density polyethylene (LDPE). In some embodiments, the polyolefin is a high-density polyethylene (HDPE). In some embodiments, the polyolefin is an ultra-high molecular weight polyethylene (UHMWPE). In some embodiments, the polyolefin is selected from LDPE, HDPE, or UHMWPE.

In some embodiments, the solution, emulsion, or suspension is disposed within a chamber of a compressible bottle. In some embodiments, the polymeric matrix is disposed between the chamber and an outlet of a compressible bottle. In some embodiments, compression of the compressible bottle passes the solution, emulsion, or suspension through the polymeric matrix to the outlet. In some embodiments, compression of the compressible bottle forms a drop at the outlet. In some embodiments, the concentration of the ophthalmic agent after passing though the polymeric matrix is at least 80%, 85%, 90%, or 95% of a concentration of the ophthalmic agent before passing through the polymeric matrix. In some embodiments, the concentration of the ophthalmic agent after passing though the polymeric matrix is at least 80% of a concentration of the ophthalmic agent before passing through the polymeric matrix. In some embodiments, the concentration of the ophthalmic agent after passing though the polymeric matrix is at least 90% of a concentration of the ophthalmic agent before passing through the polymeric matrix. In some embodiments, the concentration of the ophthalmic agent after passing though the polymeric matrix is at least 93% of the concentration of the ophthalmic agent before passing through the polymeric matrix. In some embodiments, the concentration of the ophthalmic agent after passing though the polymeric matrix is at least 95% of the concentration of the ophthalmic agent before passing through the polymeric matrix. In some embodiments, the concentration of the ophthalmic agent after passing though the polymeric matrix is at least 97% of the concentration of the ophthalmic agent before passing through the polymeric matrix. In some embodiments, the concentration of the preservative after passing though the polymeric matrix is less than 10%, 9%, 8%, 7%, 6%, 5%, 4%, 3%, 2%, or 1% of the concentration of the preservative before passing through the polymeric matrix. In some embodiments, the concentration of the preservative after passing though the polymeric matrix is less than 10% of the concentration of the preservative before passing through the polymeric matrix. In some embodiments, the concentration of the preservative after passing though the polymeric matrix is less than 5% of the concentration of the preservative before passing through the polymeric matrix. In some embodiments, the concentration of the preservative after passing though the polymeric matrix is less than 1% of the concentration of the preservative before passing through the polymeric matrix. In some embodiments, a timescale for drop formation is less than 3 seconds.

In some embodiments, the active polymeric matrix is polyvinyl alcohol crosslinked with citric acid or other suitable crosslinking agent to render it a hydrogel. In some embodiments, the active polymeric matrix is selected from crosslinked polyvinylpyrrolidone, crosslinked polyethylene oxide, crosslinked polyacrylamides, crosslinked copolymers of methacrylic acid, polyacrylic acid, or copolymers selected from poly (acrylic acid-co-acrylamide), or poly (methacrylic acid-co-acrylamide). In some embodiments, the active polymeric matrix is hydrogel prepared from polyacrylamide crosslinked with at least one crosslinking monomer selected from N,N'-methylenebis(acrylamide) (MBAM), triacrylamido triazine (TATZ), SR 351, or SR9035; and the crosslinked polyacrylamide is modified with at least one modifying monomer selected from methyl methacrylate (MAA), 2-acrylamido-2-methylpropane sulfonic acid (AMPS), 2-sulfoethyl methacrylate (SEM), acrylic acid (AA), or vinylphosphonic acid (VP). In some embodiments, the active polymeric matrix comprises one or more monomers comprising acrylamide, acrylic acid (e.g., a compound having an acrylic acid such as methacrylic acid), or acrylate, which can be crosslinked with one or more crosslinking monomers.

In some embodiments, the active polymeric matrix is hydrogel prepared from polyacrylamide crosslinked with N,N'-methylenebis(acrylamide) (MBAM); and the crosslinked polyacrylamide is modified with 2-sulfoethyl methacrylate (SEM). In some embodiments, the active polymeric matrix is hydrogel prepared from polyacrylamide crosslinked with at least one crosslinking monomer selected from N,N'-methylenebis(acrylamide) (MBAM), triacrylamido triazine (TATZ), SR 351, or SR9035; the crosslinked polyacrylamide material is isolated; and the crosslinked polyacrylamide material is modified with at least one modifying monomer selected from methyl methacrylate (MAA), 2-acrylamido-2-methylpropane sulfonic acid (AMPS), 2-sulfoethyl methacrylate (SEM), acrylic acid (AA), or vinylphosphonic acid (VP).

In some embodiments, the active polymeric matrix is hydrogel prepared from polyacrylamide crosslinked with N,N'-methylenebis(acrylamide) (MBAM; the crosslinked polyacrylamide material is isolated; and the crosslinked polyacrylamide material is modified with at least one modifying monomer selected from 2-acrylamido-2-methylpropane sulfonic acid (AMPS), or 2-sulfoethyl methacrylate (SEM). In some embodiments, the crosslinked polyacrylamide material is isolated in the form of spherical beads.

In some embodiments, the active polymeric matrix is an oxidized polyethylene, such as Honeywell A-C 395A, or the like.

In some embodiments, the inactive polymeric matrix component is a polyolefin in the form of a ground powder or a spherical bead. In some embodiments, the shape of the polyolefin particle is regular. In some embodiments, the shape of the polyolefin particle is irregular. In some embodiments, the polyolefin particle size is at least 1 micron, 10 microns, 50 microns, or 100 microns. In some embodiments, the polyolefin particle size is up to 600 microns, 700 microns, 800 microns, 900 microns, or 1000 microns. In some embodiments, the polyolefin particle size is from about 1 micron to about 1000 microns. In some embodiments, the polyolefin particle size is from about 10 microns to about 700 microns. In some embodiments, the polyolefin particle size is from about 50 microns to about 600 microns.

In some embodiments, the inactive polymeric matrix component is an inert material selected from metal or glass, wherein the inert material is in bead or powder form. In some embodiments, the inactive polymeric matrix component is an inert material coated with a surface antimicrobial material which renders the matrix resistant to bacterial or fungal growth during the storage and use.

In some embodiments, the inactive polymeric matrix component is a polyolefin having substantially no affinity for the ophthalmic agent, or combination of agents, being administered. In some embodiments, substantially no affinity means less than 0.1% of the ophthalmic agent(s) is retained. In some embodiments, substantially no affinity means less than 0.5% of the ophthalmic agent(s) is retained. In some embodiments, substantially no affinity means less than 1.0% of the ophthalmic agent(s) is retained. In some embodiments, substantially no affinity means less than 1.5% of the ophthalmic agent(s) is retained. In some embodiments, substantially no affinity means less than 2.0% of the ophthalmic agent(s) is retained. In some embodiments, substantially no affinity means less than 2.5% of the ophthalmic agent(s) is retained. In some embodiments, substantially no affinity means less than 3.0% of the ophthalmic agent(s) is retained. In some embodiments, substantially no affinity means less than 4.0% of the ophthalmic agent(s) is retained. In some embodiments, substantially no affinity means less than 5.0% of the ophthalmic agent(s) is retained.

In some embodiments, the polymeric matrix comprises an active matrix component and an inactive matrix component in a ratio of about 1% (w/w) to about 99% (w/w). In some embodiments, the polymeric matrix comprises an active matrix component and an inactive matrix component in a ratio of about 10% (w/w) to about 90% (w/w). In some embodiments, the polymeric matrix comprises an active matrix component and an inactive matrix component in a ratio of about 20% (w/w) to about 80% (w/w). In some embodiments, the polymeric matrix comprises an active matrix component and an inactive matrix component in a ratio of about 30% (w/w) to about 70% (w/w). In some embodiments, the polymeric matrix comprises an active matrix component and an inactive matrix component in a ratio of about 50% (w/w). In some embodiments, the polymeric matrix comprises an active matrix component and an inactive matrix component in a ratio of about 5% (w/w) to about 95% (w/w), about 10% (w/w) to about 90% (w/w), about 15% (w/w) to about 85% (w/w), about 20% (w/w) to about 80% (w/w), about 25% (w/w) to about 75% (w/w), about 30% to about 70% (w/w), about 35% (w/w) to about 65% (w/w), about 40% to about 60% (w/w), about 45% (w/w) to about 55% (w/w), about 50% (w/w) to about 50% (w/w), about 55% (w/w) to about 45% (w/w), about 60% (w/w) to about 40% (w/w), about 65% (w/w) to about 35% (w/w), about 70% (w/w) to about 30% (w/w), about 85% (w/w) to about 15% (w/w), about 90% (w/w) to about 10% (w/w), or about 95% (w/w) to about 5% (w/w).

In another aspect, disclosed herein is a method for administering an ophthalmic agent, comprising: providing a solution, emulsion, or suspension comprising an ophthalmic agent and a preservative in a container suitable for drop-wise dispensing; providing a polymeric matrix, wherein the polymeric matrix is configured to selectively absorb the preservative when the solution, emulsion, or suspension is passed therethrough, and wherein the polymeric matrix comprises an active matrix component and an inactive matrix component; and dispensing at least one drop of the solution, emulsion, or suspension comprising an ophthalmic agent, said solution, emulsion, or suspension having passed through the polymeric matrix. In some cases, the inactive matrix component has substantially no affinity for the ophthalmic agent or the preservative. The active polymeric matrix component can be a polymeric hydrogel. The inactive polymeric matrix component is a polyolefin in some instances. The polyolefin can be a polyethylene, polypropylene or copolymers thereof. In some cases, the polyolefin is a low-density polyethylene (LDPE). The container can be any container suitable for drop-wise dispensing such as, for example, a compressible bottle. In some instances, compression of the compressible bottle passes the solution, emulsion, or suspension through the polymeric matrix to the outlet. The dispensing step can occur as the result of compression of the compressible bottle to form a drop at the outlet. Various ophthalmic agents can be used. In some instances, the ophthalmic agent comprises latanoprost. In other cases, the ophthalmic agent comprises timolol and brimonidine. Sometimes, the ophthalmic agent comprises brimonidine. Various preservatives can be used that are removable by the polymeric matrix disclosed herein. The preservative can be an ionic preservative. The ionic preservative can be a positively charged compound. In some cases, the preservative is benzalkonium chloride. In some cases, the concentration of the preservative is less than 0.05% by weight. Sometimes, the polymeric matrix is polymeric hydrogel and the preservative is benzalkonium chloride. In some instances, the polymeric matrix comprises 2-hydroxyethylmethacrylate. In some cases, the polymeric matrix comprises tert-butyl methacrylate. The polymeric matrix can comprise one or more crosslinkers. For example, the crosslinker can be SR-9035. The solution, emulsion, or suspension can be disposed within various storage chambers or containers, for example, a chamber of a compressible bottle. In some cases, the polymeric matrix is disposed between the chamber and an outlet of a compressible bottle. In the case of a compressible bottle, compression of the compressible bottle can cause the solution, emulsion, or suspension to pass through the polymeric matrix to the outlet. The compression of the compressible bottle can form a drop at the outlet. In some cases, the concentration of the ophthalmic agent after passing though the polymeric matrix is at least 90% of a concentration of the ophthalmic agent before passing through the polymeric matrix. The concentration of the ophthalmic agent after passing though the polymeric matrix can be at least 95% of a concentration of the ophthalmic agent before passing through the polymeric matrix. Sometimes, the concentration of the ophthalmic agent after passing though the polymeric matrix is at least 97% of the concentration of the ophthalmic agent before passing through the polymeric matrix. The concentration of the preservative after passing though the polymeric matrix can be less than 10% of the concentration of the preservative before passing through the polymeric matrix. Sometimes, the concentration of the preservative after passing though the polymeric matrix is less than 5% of the concentration of the preservative before passing through the polymeric matrix. The concentration of the preservative after passing though the polymeric matrix is less than 1% of the concentration of the preservative before passing through the polymeric matrix, in some instances. The removal of the preservative can occur on a timescale for drop formation such that the preservative removing device is practical for removing a preservative from a solution, emulsion, or suspension. For example, a timescale for drop formation can be less than 3 seconds. The polymeric matrix can comprise one or more components selected from crosslinked polyvinylpyrrolidone, crosslinked polyethylene oxide, crosslinked polyacrylamides, crosslinked copolymers of methacrylic acid, polyacrylic acid, or copolymers selected from poly (acrylic acid-co-acrylamide), or poly (methacrylic acid-co- The polymeric matrix can be hydrogel prepared from polyacrylamide crosslinked with at least one crosslinking monomer selected from N,N'-methylenebis(acrylamide) (MBAM), triacrylamido triazine (TATZ), SR 351, or SR9035; and the crosslinked polyacrylamide is modified with at least one modifying monomer selected from methyl methacrylate (MAA), 2-acrylamido-2-methylpropane sulfonic acid (AMPS), 2-sulfoethyl methacrylate (SEM), acrylic acid (AA), or vinylphosphonic acid (VP). The polymeric matrix can be hydrogel prepared from polyacrylamide crosslinked with N,N'-methylenebis(acrylamide) (MBAM); and the crosslinked polyacrylamide is modified with 2-sulfoethyl methacrylate (SEM). In some cases, the polymeric matrix is hydrogel prepared from polyacrylamide crosslinked with at least one crosslinking monomer selected from N,N'-methylenebis(acrylamide) (MBAM), triacrylamido triazine (TATZ), SR 351, or SR9035; the crosslinked polyacrylamide material is isolated; and the crosslinked polyacrylamide material is modified with at least one modifying monomer selected from methyl methacrylate (MAA), 2-acrylamido-2-methylpropane sulfonic acid (AMPS), 2-sulfoethyl methacrylate (SEM), acrylic acid (AA), or vinylphosphonic acid (VP). Sometimes, the polymeric matrix is hydrogel prepared from polyacrylamide crosslinked with N,N'-methylenebis (acrylamide) (MBAM); the crosslinked polyacrylamide material is isolated; and the crosslinked polyacrylamide material is modified with at least one modifying monomer selected from 2-acrylamido-2-methylpropane sulfonic acid (AMPS), or 2-sulfoethyl methacrylate (SEM).

In another aspect, disclosed herein is a preservative removing device, comprising: a polymeric matrix, wherein the polymeric matrix is configured to selectively absorb a preservative when a solution, emulsion, or suspension comprising an ophthalmic agent and a preservative is passed therethrough, and wherein the polymeric matrix comprises an active matrix component and an inactive matrix component. In some cases, the inactive matrix component has substantially no affinity for the ophthalmic agent or the preservative. The active polymeric matrix component can be a polymeric hydrogel. The inactive polymeric matrix component can be a polyolefin. The polyolefin can be a polyethylene, polypropylene or copolymers thereof. In some instances, the polyolefin is a low-density polyethylene (LDPE). Sometimes, the solution, emulsion, or suspension comprising an ophthalmic agent and a preservative is contained in a container suitable for drop-wise dispensing. In some cases, the inactive matrix component has substantially no affinity for the ophthalmic agent or the preservative. The active polymeric matrix component can be a polymeric hydrogel. The inactive polymeric matrix component is a polyolefin in some instances. The polyolefin can be a polyethylene, polypropylene or copolymers thereof. In some cases, the polyolefin is a low-density polyethylene (LDPE). The container can be any container suitable for drop-wise dispensing such as, for example, a compressible bottle. In some instances, compression of the compressible bottle passes the solution, emulsion, or suspension through the polymeric matrix to the outlet. The dispensing step can occur as the result of compression of the compressible bottle to form a drop at the outlet. Various ophthalmic agents can be used. In some instances, the ophthalmic agent comprises latanoprost. In other cases, the ophthalmic agent comprises timolol and brimonidine. Sometimes, the ophthalmic agent comprises brimonidine. Various preservatives can be used that are removable by the polymeric matrix disclosed herein. The preservative can be an ionic preservative. The ionic preservative can be a positively charged compound. In some cases, the preservative is benzalkonium chloride. In some cases, the concentration of the preservative is less than 0.05% by weight. Sometimes, the polymeric matrix is polymeric hydrogel and the preservative is benzalkonium chloride. In some instances, the polymeric matrix comprises 2-hydroxyethylmethacrylate. In some cases, the polymeric matrix comprises tert-butyl methacrylate. The polymeric matrix can comprise one or more crosslinkers. For example, the crosslinker can be SR-9035. The solution, emulsion, or suspension can be disposed within various storage chambers or containers, for example, a chamber of a compressible bottle. In some cases, the polymeric matrix is disposed between the chamber and an outlet of a compressible bottle. In the case of a compressible bottle, compression of the compressible bottle can cause the solution, emulsion, or suspension to pass through the polymeric matrix to the outlet. The compression of the compressible bottle can form a drop at the outlet. In some cases, the concentration of the ophthalmic agent after passing though the polymeric matrix is at least 90% of a concentration of the ophthalmic agent before passing through the polymeric matrix. The concentration of the ophthalmic agent after passing though the polymeric matrix can be at least 95% of a concentration of the ophthalmic agent before passing through the polymeric matrix. Sometimes, the concentration of the ophthalmic agent after passing though the polymeric matrix is at least 97% of the concentration of the ophthalmic agent before passing through the polymeric matrix. The concentration of the preservative after passing though the polymeric matrix can be less than 10% of the concentration of the preservative before passing through the polymeric matrix. Sometimes, the concentration of the preservative after passing though the polymeric matrix is less than 5% of the concentration of the preservative before passing through the polymeric matrix. The concentration of the preservative after passing though the polymeric matrix is less than 1% of the concentration of the preservative before passing through the polymeric matrix, in some instances. The removal of the preservative can occur on a timescale for drop formation such that the preservative removing device is practical for removing a preservative from a solution, emulsion, or suspension. For example, a timescale for drop formation can be less than 3 seconds. The polymeric matrix can comprise one or more components selected from crosslinked polyvinylpyrrolidone, crosslinked polyethylene oxide, crosslinked polyacrylamides, crosslinked copolymers of methacrylic acid, polyacrylic acid, or copolymers selected from poly (acrylic acid-co-acrylamide), or poly (methacrylic acid-co- The polymeric matrix can be hydrogel prepared from polyacrylamide crosslinked with at least one crosslinking monomer selected from N,N'-methylenebis(acrylamide) (MBAM), triacrylamido triazine (TATZ), SR 351, or SR9035; and the crosslinked polyacrylamide is modified with at least one modifying monomer selected from methyl methacrylate (MAA), 2-acrylamido-2-methylpropane sulfonic acid (AMPS), 2-sulfoethyl methacrylate (SEM), acrylic acid (AA), or vinylphosphonic acid (VP). The polymeric matrix can be hydrogel prepared from polyacrylamide crosslinked with N,N'-methylenebis(acrylamide) (MBAM); and the crosslinked polyacrylamide is modified with 2-sulfoethyl methacrylate (SEM). In some cases, the polymeric matrix is hydrogel prepared from polyacrylamide crosslinked with at least one crosslinking monomer selected from N,N'-methylenebis(acrylamide) (MBAM), triacrylamido triazine (TATZ), SR 351, or SR9035; the crosslinked polyacrylamide material is isolated; and the crosslinked polyacrylamide material is modified with at least one modifying monomer selected from methyl methacrylate (MAA), 2-acrylamido-2-methylpropane sulfonic acid (AMPS), 2-sulfoethyl methacrylate (SEM), acrylic acid (AA), or vinylphosphonic acid (VP). Sometimes, the polymeric matrix is hydrogel prepared from polyacrylamide crosslinked with N,N'-methylenebis(acrylamide) (MBAM); the crosslinked polyacrylamide material is isolated; and the crosslinked polyacrylamide material is modified with at least one modifying monomer selected from 2-acrylamido-2-methylpropane sulfonic acid (AMPS), or 2-sulfoethyl methacrylate (SEM).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm or 0.1 mm of a given value or range.

As used herein, the terms "comprises," "comprising," or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "user", "subject" or "patient" are used interchangeably. As used herein, the terms "subject" and "subjects" refers to an animal (e.g., birds, reptiles, and mammals), a mammal including a primate (e.g., a monkey, chimpanzee, and a human) and a non-primate (e.g., a camel, donkey, zebra, cow, pig, horse, cat, dog, rat, and mouse). In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100. In some embodiments, the subject or patient is a pig. In certain embodiments, the pig is 0 to 6 months old, 6 to 12 months old, 1 to 5 years old, 5 to 10 years old or 10 to 15 years old. The natural lifespan of a pig is 10-15 years.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms may be based on objective or subjective parameters; including the results of a physical examination, neuropsychiatric exams, and/or a psychiatric evaluation. The term "treating" and conjugations thereof, include prevention of an injury, pathology, condition, or disease.

In some embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of a "therapeutically effective amount" is an amount sufficient to contribute to the treatment, prevention, or reduction of a symptom or symptoms of a disease, which could also be referred to as a "therapeutically effective amount." A "reduction of" a symptom or symptoms (and grammatical equivalents of this phrase) means decreasing of the severity or frequency of the symptom(s), or elimination of the symptom(s). The exact amounts may depend on the purpose of the treatment and may be ascertainable by one skilled in the art using known techniques.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

In an aspect, a method for administering an ophthalmic agent is provided. The method may comprise: providing a solution, emulsion, or suspension comprising an ophthalmic agent, and a preservative; and providing a polymeric matrix, wherein the polymeric matrix is configured to selectively absorb the preservative when the solution, emulsion, or suspension is passed therethrough, and wherein the polymeric matrix comprises an active matrix component and an inactive matrix component. The inactive matrix component has substantially no affinity for the ophthalmic agent or the preservative.

Our prior investigations have developed active hydrogel polymeric materials that are effective in the absorption of preservatives, such as benzalkonium chloride (BAK), from formulations of ophthalmic drugs. Surprisingly, it has been found that creating a physical blend of the active hydrogel polymer with another inactive polymer, such as polyolefin having no affinity for the ophthalmic agent or preservative, provides a polymeric matrix with improved drug delivery properties in several ways. First, the flow through the tip is improved requiring less finger pressure to the bottle for the user to create drops to the eye. Second, absorption of the ophthalmic agent by the active hydrogel is reduced and results in consistent delivery of ophthalmic agent at the intended concentration.

When a solution of ophthalmic agent and BAK are passed through an active hydrogel in the tip of a system similar to that described herein, the first 1-15 drops that are expressed may have a concentration of ophthalmic agent higher, or lower, than the stated concentration of the drug in the dispensing bottle. The stated concentration is the desired concentration of the drug that is useful and most desirable for efficacy of the drug in the eye. It is therefore beneficial and desired that all drops expressed from the bottle have as close to the stated concentration as possible. It has been found unexpectedly that using an additional matrix component that is totally non-absorbing of the drug provides a drug concentration in the drops closer to the stated concentration in the bottle. It has also been found, surprisingly, that the effect of adding the inactive matrix component polymer to the active hydrogel polymer can be to either raise or lower the concentration in the drops to be closer to the label concentration when compared to the preservative removal matrix without the inactive component. It has also been found that this blend of the active hydrogel with the non-absorbing, inactive polymer improves the flow through the tip in such a way as to provide a system requiring a lower amount of squeeze pressure to the bottle when expressing the drops.

In some embodiments, the polymeric matrix comprising an active matrix component and an inactive matrix component is suitable for selectively removing a preservative from a solution, emulsion, or suspension comprising an ophthalmic agent and the preservative while allowing the ophthalmic agent to pass through. In some embodiments, the polymeric matrix comprising an active matrix component and an inactive matrix component allows the solution, emulsion, or suspension comprising the ophthalmic agent to pass through to form a plurality of drops having concentrations with a lower standard deviation as compared to a polymeric matrix having only the active matrix component. In some embodiments, the plurality of drops are the first 3, 5, 10, 15, 20, or 25 drops that form as the solution, emulsion, or suspension passes through the polymeric matrix. In some embodiments, the polymeric matrix comprising the active matrix component and the inactive matrix component produces drops having concentrations with a standard deviation that is at least about 10%, 20%, 30%, 40%, 50%, 60%, 70%, 80%, 90%, or 100% lower than a standard deviation for drops produced by a polymeric matrix having only the active matrix component.

Embodiments of the present disclosure provide a preservative removing device. The preservative removing device may comprise (1) a solution, emulsion, or suspension comprising an ophthalmic agent, and a preservative; and (2) a polymeric matrix, wherein the polymeric matrix is configured to selectively absorb the preservative when the solution, emulsion, or suspension is passed therethrough.

Figure 1:
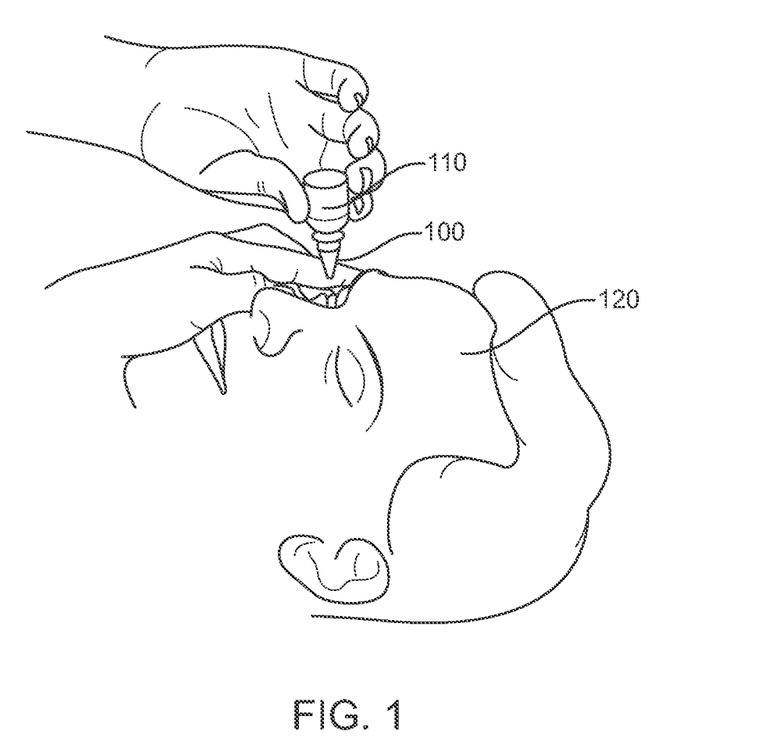
FIG. 1 illustrates a system for providing an ophthalmic agent, in accordance with some embodiments.

FIG. 1 illustrates a system for providing an ophthalmic agent, in accordance with some embodiments. The system may comprise a preservative removing device 100 disposed within a neck of a compressible bottle 110. A pressure may be applied by a user 120 (e.g. a patient, a subject) to compressible bottle 110 to pass a solution, emulsion, or suspension through a preservative removing device to thereby deliver an ophthalmic agent to an eye.

Figure 2A:
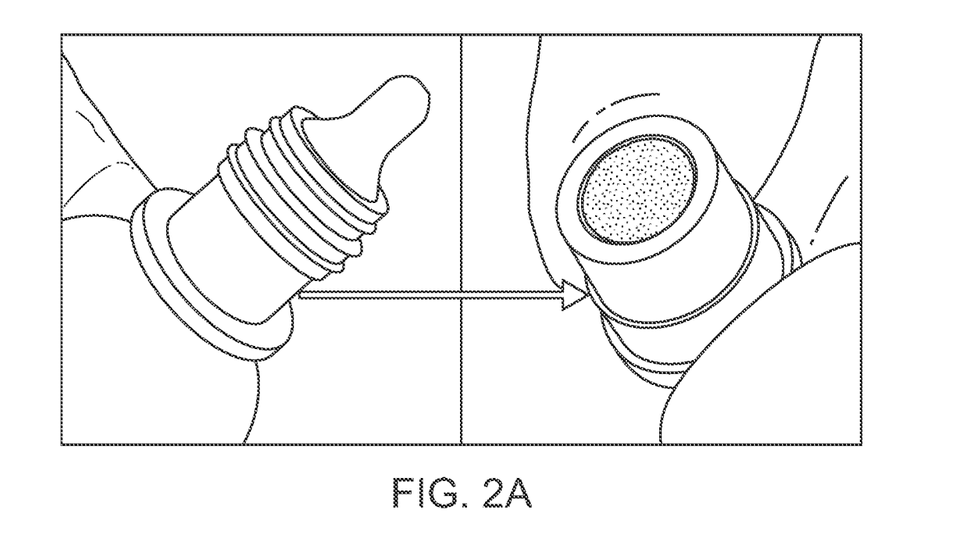
FIG. 2A illustrates an eye drop bottle comprising a matrix in a removable cap, in accordance with some embodiments.
Figure 2B:
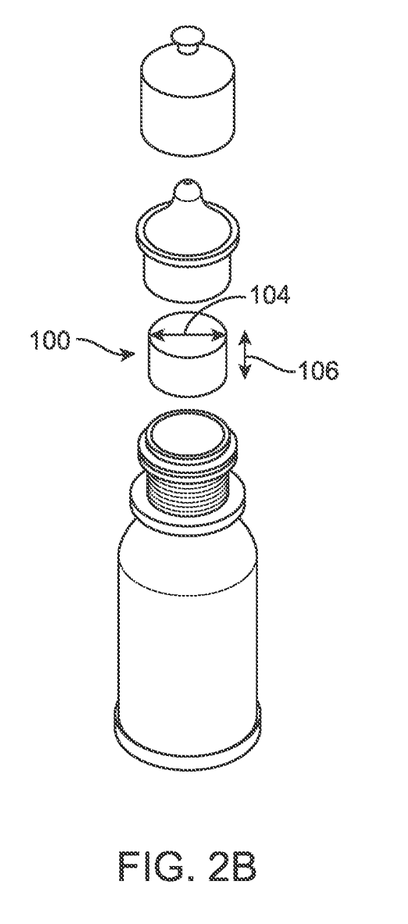
FIG. 2B illustrates a compressible bottle comprising a matrix, in accordance with some embodiments.
Figure 2C:
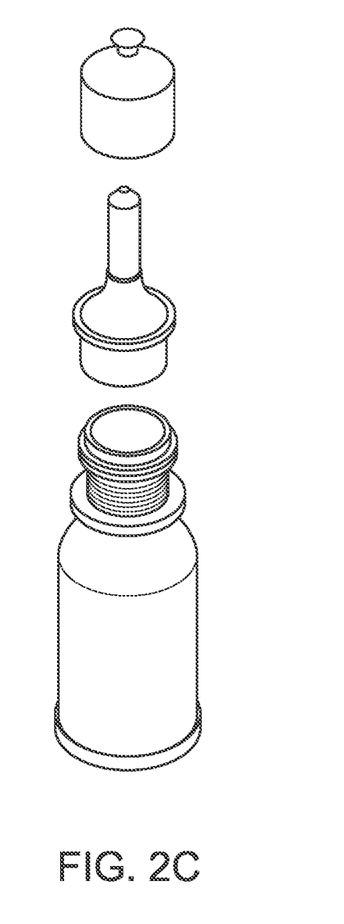
FIG. 2C illustrates a compressible bottle comprising a matrix in the neck of a nozzle, in accordance with some embodiments.

FIG. 2A illustrates an eye drop bottle comprising a matrix in a removable cap, in accordance with some embodiments. FIG. 2B illustrates a compressible bottle comprising a matrix, in accordance with some embodiments. FIG. 2C illustrates a compressible bottle comprising a matrix in the neck of a nozzle, in accordance with some embodiments. A porous preservative removing device may be situated in the neck of the eye drop bottle leading to the drop exit. In some embodiments, the matrix may be situated in a section of the tip of the eye drop bottle. A tip may be included in the bottle to allow a matrix to be positioned therein. The preservative removing device can be separate filter that is attached to the formulation dispensing unit through a suitable connector for use. The preservative removing device may comprise a portion of a multi-dosing device for delivery of an ophthalmic solution. A multi-dosing device may comprise a compressible bottle that has an outlet extension containing the preservative removing device. When the hydrophilic polymeric gel is dry, it may have dimensions smaller than the internal dimensions of the outlet extension but may have dimensions larger than the internal dimensions of the outlet extension when swollen with the ophthalmic solution. A preservative removing device may self-support within the compressible bottle. A preservative removing device may be press fit into the bottle. A preservative removing device may be held within a secondary container (e.g. a sachet) within the compressible bottle.

Solution, Emulsion, or Suspension

Provided herein are ophthalmic formulations comprising an ophthalmic agent and a preservative. In some embodiments, ophthalmic formulations provided herein are solutions, emulsions, and/or suspensions of an ophthalmic agent and a preservative. In some embodiments, a solution, emulsion, or suspension may be used in any of the methods described herein. The solution, emulsion, or suspension may additionally comprise one or more pharmaceutically acceptable excipients.

In some embodiments, a composition of therapeutic agent, and a preservative may be used for the treatment of a therapeutic disorder such as, dry eye, bacterial infection, glaucoma, hypertension, inflammation, allergic conjunctivitis, hypotrichosis of the eyelashes, fungal infection, etc. Additionally, or alternatively, a composition of a preservative and a therapeutic agent, may be used during a preventative, diagnostic, or therapeutic ophthalmological procedure, for example, local anesthetic, pupil dilation, etc. A solution, emulsion, or suspension administered to the eye may be administered topically, for example, with an eye drop. In some embodiments, the compounds, or salts thereof, of the disclosure with low aqueous solubility may be formulated as aqueous suspensions.

Ophthalmic Agent

Embodiments of the present disclosure provide an ophthalmic agent for delivery to an eye. In some embodiments, the disclosure provides solutions, emulsions, or suspensions of a preservative and an ophthalmic agent. Ophthalmic agents may comprise compounds and salts, for use in the treatment of ophthalmic diseases. Optionally, in any embodiment, the solution, emulsion, or suspension may additionally comprise one or more pharmaceutically acceptable excipients. The disclosed compounds and salts can be used, for example, for the treatment or prevention of vision disorders and/or for use during ophthalmological procedures for the prevention and/or treatment of ophthalmic disorders. The flowing list of examples is not intended to be limiting.

An ophthalmic agent may be integrated into a fluid, which may flow from a container to an eye through an outlet of a compressible bottle. Example ophthalmic agents which may be used in conjunction with a compressible bottle include but are not limited to: timolol, dorzolamide, dexamethasone phosphate, dexamethasone, betimol, olopatadine, brimonidine, tetrahydrozoline, latanoprostene bunod, latanoprost, bimatoprost, travoprost and combinations of any two or more thereof. Ophthalmic agents may comprise brand name drugs and formulations including, but not limited to, Timoptic, Xalatan, Combigan, Lumigan, Pataday, Pazeo, Trusopt, Cosopt, Alphagan, Visine, Vyzulta, or Vesneo. The ophthalmic agents may be dissolved in aqueous solution. The solution may be sterilized and buffered to appropriate pH. In some embodiments, the solution may comprise inactive ingredients such as sodium chloride, sodium citrate, hydroxyethyl cellulose, sodium phosphate, citric acid, sodium dihydrogen phosphate, polyoxyl 40 hydrogenated castor oil, tromethamine, boric acid, mannitol, glycerine edetate disodium, sodium hydroxide, and/or hydrochloric acid. In some embodiments, the fluid comprises a preservative in addition to an ophthalmic agent. Example preservatives include but are not limited to: benzalkonium chloride (BAK), alcohols, parabens, methyl paraben, polyparaben, EDTA, chlorhexidine, quaternary ammonium compounds, Purite®, stabilized oxychloro complexes, Sofzia®, sorbic acid, Sodium perborate, polyquaternium-1, chlorobutanol, cetrimonium chloride, edetate disodium, etc.

In some embodiments the ophthalmic agent is latanoprost. In some embodiments the ophthalmic agent is bimatoprost. In some embodiments the ophthalmic agent is travoprost. In some embodiments the ophthalmic agent is latanoprost and the preservative is benzalkonium chloride (BAK). In some embodiments the ophthalmic agent is bimatoprost and the preservative is benzalkonium chloride (BAK). In some embodiments the ophthalmic agent is travoprost and the preservative is benzalkonium chloride (BAK).

In some embodiments the ophthalmic agent is brimonidine. In some embodiments the ophthalmic agents are brimonidine and timolol. In some embodiments the ophthalmic agent is brimonidine and the preservative is benzalkonium chloride (BAK). In some embodiments the ophthalmic agents are brimonidine and timolol, and the preservative is benzalkonium chloride (BAK).

In some embodiments, the ophthalmic agent comprises latanoprost, bimatoprost, dexamethasone, cyclosporine or travoprost, or any prostaglandin analog drug. In some embodiments, the concentration of the ophthalmic agent is less than 200 millimolar. In some embodiments, the concentration of the ophthalmic agent is less than 0.05% by weight. In some embodiments, the preservative is benzalkonium chloride. In some embodiments, the concentration of the preservative is less than 0.05% by weight.

Ophthalmic agents for the treatment of, for example, dry eye, bacterial infection, glaucoma, hypertension, inflammation, allergic conjunctivitis, hypotrichosis of the eyelashes, fungal infection, etc. and ophthalmic agents used for local anesthetic, pupil dilation, etc. may be administered to a patient as a solution, emulsion, or suspension delivered to an eye topically via a compressible bottle, a dropper bottle, or similar delivery mechanism. The solution, emulsion, or suspension may be subject to contamination such as microbial, fungal, or particulate contamination, which may be adverse to patient health. In order to prevent such contamination a preservative may be added to the solution, emulsion, or suspension; however, patient exposure to preservatives may have adverse effects to eye health. It may be advantageous to limit patient exposure to preservative by providing a preservative removing device which may remove a preservative from the solution, emulsion, or suspension.

In some embodiments, the ophthalmic agent to be dispensed comprises an active ingredient selected from cyclosporine and lifitegrast. In such embodiments, the ophthalmic agent may be an active ingredient in the treatment of dry eye.

In some embodiments, the ophthalmic agent to be dispensed comprises an active ingredient selected from sulfacetamide sodium, ofloxacin, gatifloxacin, ciprofloxacin, moxifloxacin, tobramycin, levofloxacin, prednisolone acetate, polymyxin B sulfate, and trimethoprim. In some embodiments, the ophthalmological formulation to be dispensed comprises the active ingredients sulfacetamide sodium and prednisolone acetate. In some embodiments, the ophthalmological formulation to be dispensed comprises the active ingredients polymyxin B sulfate and trimethoprim. In such embodiments, the ophthalmic agent may be an active ingredient in the treatment of a bacterial infection.

In some embodiments, the ophthalmic agent to be dispensed comprises an active ingredient selected from brimonidine tartrate, bimatoprost, levobunolol hydrochloride, brinzolamide, betaxolol hydrochloride, pilocarpine hydrochloride, apraclonidine, travoprost, timolol maleate, latanoprost, dorzolamide hydrochloride, timolol maleate, and tafluprost. In some embodiments, the ophthalmological formulation to be dispensed comprises the active ingredients brimonidine tartrate and timolol maleate. In some embodiments, the ophthalmological formulation to be dispensed comprises the active ingredients brinzolamide and brimonidine tartrate. In such embodiments, the ophthalmic agent may be an active ingredient in the treatment of glaucoma or hypertension.

In some embodiments, the ophthalmic agent to be dispensed comprises an active ingredient selected from ketorolac tromethamine, fluorometholone, prednisolone acetate, difluprednate, fluorometholone acetate, nepafenac, dexamethasone, diclofenac sodium, bromfenac, gentamicin, tobramycin, neomycin, and polymyxin B sulfate. In some embodiments, the ophthalmological formulation to be dispensed comprises the active ingredients gentamicin and prednisolone acetate. In some embodiments, the ophthalmological formulation to be dispensed comprises the active ingredients tobramycin and dexamethasone. In some embodiments, the ophthalmological formulation to be dispensed comprises the active ingredients neomycin, polymyxin B sulfate and dexamethasone. In such an embodiment, the ophthalmic agent may be an active ingredient in the treatment of inflammation.

In some embodiments, the ophthalmic agent to be dispensed comprises an active ingredient selected from nedocromil sodium, epinastine HCl, alcaftadine, lodoxamide tromethamine, emedastine difumarate, and olopatadine hydrochloride. In such embodiments, the ophthalmic agent may be an active ingredient in the treatment of allergic conjunctivitis.

In some embodiments, the ophthalmic agent to be dispensed comprises an active ingredient selected from proparacaine hydrochloride and tetracaine hydrochloride. In such embodiments, the ophthalmic agent may be a local anesthetic.

In some embodiments, the ophthalmic agent to be dispensed comprises an active ingredient selected from cyclopentolate hydrochloride, atropine sulfate, and tropicamide. In some embodiments, the ophthalmological formulation to be dispensed comprises the active ingredients cyclopentolate hydrochloride and phenylephrine hydrochloride. In such embodiments, the ophthalmic agent may dilate pupils.

In some embodiments, the ophthalmic agent to be dispensed comprises the active ingredient natamycin. In such embodiments, the ophthalmic agent may be an active ingredient in the treatment of fungal infection.

In some embodiments, the ophthalmic agent to be dispensed comprises an active ingredient selected from lipoic acid choline ester chloride, rebamipide, pilocarpine, ketorolac, aceclidine, tropicamide, sodium hyaluronate, diclofenac sodium, pilocarpine HCl, and ketorolac. In some embodiments, the ophthalmological formulation to be dispensed comprises the active ingredients aceclidine and tropicamide. In some embodiments, the ophthalmological formulation to be dispensed comprises the active ingredients sodium hyaluronate and diclofenac sodium and pilocarpine HCl. In some embodiments, the ophthalmological formulation to be dispensed comprises the active ingredients pilocarpine and ketorolac. In such embodiments, the ophthalmic agent may be an active ingredient in the treatment of presbyopia.

In some embodiments, solutions, emulsions, or suspensions of the disclosure comprise a compound or salt of any ophthalmic agent of the present disclosure, wherein the compound or salt of the ophthalmic agent is largely free of impurities, such as at least about 80 wt % pure, at least about 81% pure, at least about 82% pure, at least about 83% pure, at least about 84% pure, at least about 85% pure, at least about 86% pure, at least about 87% pure, at least about 88% pure, at least about 89% pure, at least about 90% pure, at least about 91% pure, at least about 92% pure, at least about 93% pure, at least about 94% pure, at least about 95% pure, at least about 96% pure, at least about 97% pure, at least about 98% pure, at least about 99% pure, at least about 99.1% pure, at least about 99.2% pure, at least about 99.3% pure, at least about 99.4% pure, at least about 99.5% pure, at least about 99.6% pure, at least about 99.7% pure, at least about 99.8% pure, or at least about 99.9% pure.

In some embodiments, solutions, emulsions, or suspensions of the disclosure comprise a compound or salt of any ophthalmic agent of the present disclosure, wherein the ophthalmic agent is about 70% to about 99.99%, about 80% to about 99.9%, about 85% to about 99%, about 90% to about 99%, about 95% to about 99%, about 97% to about 99%, about 98% to about 99%, about 98% to about 99.9%, about 99% to about 99.99%, about 99.5% to about 99.99%, about 99.6% to about 99.99%, about 99.8 to about 99.99%, or about 99.9% to about 99.99% free of impurities.

The amount of the compound or salt of the ophthalmic agent in a solution, emulsion, or suspension of the present disclosure can be measured as a percentage of mass per volume. In some embodiments, a solution, emulsion, or suspension such as an aqueous solution of the disclosure, comprises from about 0.05 wt % to about 10 wt % of the compound or salt of any of the ophthalmic agents disclosed herein. In some embodiments, a solution, emulsion, or suspension such as an aqueous solution of the disclosure, comprises about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4 wt %, about 4.1 wt %, about 4.2 wt %, about 4.3 wt %, about 4.4 wt %, about 4.5 wt %, about 5 wt %, about 6 wt %, about 7 wt %, about 8 wt %, about 9 wt %, or about 10 wt % of a compound or salt of the ophthalmic agent described herein.

A compound or salt of the ophthalmic agent described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 nM, about 30 µM, about 40 µM, about 50 µM, about 60 µM, about 70 µM, about 80 µM, about 90 nM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 nM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of an ophthalmic agent described herein may be present in a solution, emulsion, or suspension within a range of concentrations, the range being defined by an upper and lower value selected from any of the preceding concentrations. For example, the compound or salt of an ophthalmic agent of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Preservative

The present disclosure provides formulations comprising one or more preservatives for solutions, emulsions, or suspensions of ophthalmic agents of the present disclosure. Preservatives may comprise compounds and salts, for use as preservatives for solutions, emulsions, or suspensions of ophthalmic agents. The one or more preservatives may for example prevent microbial and/or fungal growth. The one or more preservatives may for example prevent physical or chemical deterioration of an ophthalmic agent.

Non-limiting examples of preservative agents include benzalkonium chloride, ethylenediaminetetraacetic acid (EDTA), chlorobutanol, phenylmercuric acetate, phenylmercuric nitrate, chlorhexidine acetate, thimerosal, benzethonium chloride, sorbic acid, alcohols, parabens (e.g., methylparaben, polyparaben), chlorhexidine, quaternary ammonium compounds, cetrimonium bromide, cetramide, cetyltrimethylammonium bromide, hexadecyltrimethylammonium bromide polyquaternium-1 (Polyquad®), stabilized oxychloro complexes (Purite®), solutions of borate, sorbitol, propylene glycol, and zinc (Sofzia®), sodium perborate (GenAqua®), cetrimonium chloride, edetate disodium, etc. In some embodiments, a formulation of the disclosure comprises the preservative of quaternary ammonium compounds. In some embodiments the preservative is benzalkonium chloride (BAK).

In some embodiments, the particulate plug may further include a preservative removing compound or a preservative deactivating compound. Preservative removing or deactivating compounds can decrease toxicity of a formulation to be delivered through typical separation methods including, but not limited to, adsorption, ion exchange, chemical precipitation, or solvent extraction. Preservative removing or deactivating compounds can include, but are not limited to, activated charcoal, antioxidants, ethylenediaminetetraacetic acid (EDTA), anionic hydrogels, cationic compounds, neutralizing agents, or combinations thereof.

The Purite® preservative system includes Stabilized Oxychloro Complex (SOC), a combination of chlorine dioxide, chlorite, and chlorate. When exposed to light, SOC dissociates into water, oxygen, sodium, and chlorine free radicals which cause oxidation of intracellular lipids and glutathione, interrupting vital enzymes for cell function and maintenance. For preservatives such as Purite® which produce chlorine free radicals, the particulate plug of the disclosure can include a material that has a high affinity for free radicals such as activated charcoal or antioxidants such as vitamin E.

The SofZia® preservative system in Travatan Z (Alcon Laboratories, Fort Worth, Tex.) contains borate, sorbitol, propylene glycol, and zinc. Without intending to be bound by theory, it is believed that the preservative effect is from a combination of borate and zinc. For preservatives including borate and zinc, such as SofZia®, the particulate plug of the disclosure can include a metal chelating agent such as EDTA, anionic hydrogels that can extract cationic zinc through electrostatic interactions, cationic hydrogels or resins that can extract anionic borate ions through electrostatic interactions, or a neutralizing agent that can neutralize boric acid.

In some embodiments, solutions, emulsions, or suspensions of the disclosure comprise a compound or salt of any preservative of the present disclosure, wherein the compound or salt of the preservative is largely free of impurities, such as at least about 80% pure, at least about 81% pure, at least about 82% pure, at least about 83% pure, at least about 84% pure, at least about 85% pure, at least about 86% pure, at least about 87% pure, at least about 88% pure, at least about 89% pure, at least about 90% pure, at least about 91% pure, at least about 92% pure, at least about 93% pure, at least about 94% pure, at least about 95% pure, at least about 96% pure, at least about 97% pure, at least about 98% pure, at least about 99% pure, at least about 99.1% pure, at least about 99.2% pure, at least about 99.3% pure, at least about 99.4% pure, at least about 99.5% pure, at least about 99.6% pure, at least about 99.7% pure, at least about 99.8% pure, or at least about 99.9% pure.

In some embodiments, solutions, emulsions, or suspensions of the disclosure comprise a compound or salt of any preservative of the present disclosure, wherein the preservative is about 70% to about 99.99%, about 80% to about 99.9%, about 85% to about 99%, about 90% to about 99%, about 95% to about 99%, about 97% to about 99%, about 98% to about 99%, about 98% to about 99.9%, about 99% to about 99.99%, about 99.5% to about 99.99%, about 99.6% to about 99.99%, about 99.8 to about 99.99%, or about 99.9% to about 99.99% free of impurities.

The amount of the compound or salt of the preservative in a solution, emulsion, or suspension of the present disclosure can be measured as a percentage of mass per volume. In some embodiments, a solution, emulsion, or suspension such as an aqueous solution of the disclosure, comprises from about 0.05 wt % to about 10 wt % of the compound or salt of any of the preservatives disclosed herein. In some embodiments, a solution, emulsion, or suspension such as an aqueous solution of the disclosure, comprises about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4 wt %, about 4.1 wt %, about 4.2 wt %, about 4.3 wt %, about 4.4 wt %, about 4.5 wt %, about 5 wt %, about 6 wt %, about 7 wt %, about 8 wt %, about 9 wt %, or about 10 wt % of a compound or salt of the preservative described herein.

A compound or salt of the preservative described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a preservative described herein may be present in a solution, emulsion, or suspension within a range of concentrations, the range being defined by an upper and lower value selected from any of the preceding concentrations. For example, the compound or salt of an preservative of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Excipients

Devices and methods of the present disclosure may comprise formulating the solution, emulsion, or suspension with one or more inert, pharmaceutically-acceptable excipients. Liquid compositions include, for example, solutions in which a compound is dissolved, emulsions comprising a compound, or a solution containing liposomes or micelles comprising an ophthalmic agent as disclosed herein. These compositions can also contain minor amounts of nontoxic, auxiliary substances, such as wetting or emulsifying agents, pH buffering agents, tonicity agents and other pharmaceutically-acceptable additives.

In some embodiments, solutions, emulsions, or suspensions of the present disclosure further comprise one or more physiologically acceptable carriers including excipients and auxiliaries which facilitate processing of the pharmaceutical agent into preparations which are used pharmaceutically. Proper formulation is dependent upon the route of administration chosen.

Pharmaceutically acceptable carriers include, for example, aqueous solutions such as water or physiologically buffered saline or other solvents or vehicles such as glycols, glycerol, oils such as olive oil, or organic esters. The excipients can be chosen, for example, to effect delayed release of an agent or to selectively target one or more cells, tissues or organs. The composition can also be present in a solution suitable for topical administration, such as an eye drop.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, hydroxypropyl methylcellulose, hypromellose, Methocel, methyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In some embodiments, the solutions, emulsions, or suspensions of the disclosure may include one or more additional excipients. The amount of the excipient in a pharmaceutical formulation of the disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 60%, about 70%, about 80%, about 90%, about 100%, about 200%, about 300%, about 400%, about 500%, about 600%, about 700%, about 800%, about 900%, or about 1000% by mass of the compound in the solution, emulsion, or suspension. The amount of the excipient in a solution, emulsion, or suspension of the disclosure can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass of the compound in the solution, emulsion, or suspension.

The amount of the excipient in a solution, emulsion, or suspension of the present disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form. The amount of the excipient in a solution, emulsion, or suspension can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass or by volume of the unit dosage form.

The ratio of a compound of an ophthalmic agent of the present disclosure to an excipient in a pharmaceutical formulation of the present disclosure can be about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1 about 30:about 1, about 25:about 1, about 20:about 1, about 15:about 1, about 10:about 1, about 9:about 1, about 8:about 1, about 7:about 1, about 6:about 1, about 5:about 1, about 4:about 1, about 3:about 1, about 2:about 1, about 1:about 1, about 1:about 2, about 1:about 3, about 1:about 4, about 1:about 5, about 1:about 6, about 1:about 7, about 1:about 8, about 1:about 9, or about 1:about 10. The ratio of a compound of an ophthalmic agent to an excipient in a solution, emulsion, or suspension of the present disclosure can be within the range of between about 100:about 1 and about 1 to about 10, between about 10:about 1 and about 1:about 1, between about 5:about 1 and about 2:about 1.

In some embodiments, a solution, emulsion, or suspension of the present disclosure comprises an agent for adjusting the pH of the formulation. In some embodiments, the agent for adjusting the pH could be an acid, e.g., hydrochloric acid or boric acid, or a base, e.g., sodium hydroxide or potassium hydroxide. In some embodiments, the agent for adjusting the pH is an acid such as boric acid. The formulation may comprise about 0.05 wt % to about 5 wt %, about 0.1% to about 4%, about 0.1% to about 3 wt %, about 0.1 wt % to about 2 wt %, or about 0.1 wt % to about 1 wt % of an agent for adjusting the pH.

Solutions, emulsions, or suspensions of the disclosure can be formulated at any suitable pH. In some embodiments, the pH of the solution emulsion or suspension is about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9 pH units. In some embodiments, the pH of the solution, emulsion, or suspension is from about 4 to about 10, about 4.75 to about 7.40, about 5 to about 9, about 6 to about 8, about 6.5 to about 8, about 7 to about 8, about 7.2 to about 8, about 7.2 to about 7.8, about 7.3 to about 7.5, or about 7.35 to about 7.45. In some embodiments the pH of the solution, emulsion, or suspension is about 7.4.

In some embodiments, the addition of an excipient to a pharmaceutical formulation of the present disclosure can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical formulation of the present disclosure can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%. Examples of ranges which the viscosity change falls within can be created by combining any two of the preceding percentages. For example the addition of an excipient can increase or decrease the viscosity of the composition by 5% to 99%, by 10% to 95%, by 20% to 70% or by 35% to 55%.

In some embodiments, an excipient that increases a viscosity may comprise polyvinyl alcohol, poloxamers, hyaluronic acid, carbomers, and polysaccharides, that is, cellulose derivatives, hydroxymethyl cellulose, hypromellose, Methacel, gellan gum, and xanthan gum. In some embodiments, an excipient that increases mucoadhesive properties may be added. Excipients that increase mucoadhesion may include polyacrylic acid, hyaluronic acid, sodium carboxymethyl cellulose, lectins, and chitosan.

In some embodiments, solutions, emulsions, or suspensions of the present disclosure further comprise an agent for adjusting the osmolarity of the solution, emulsion, or suspension, e.g., mannitol, sodium chloride, sodium sulfate, dextrose, potassium chloride, glycerin, propylene glycol, calcium chloride, and magnesium chloride. In some embodiments, the solution, emulsion, or suspension comprises from about 0.1 wt % to about 10 wt %, about 0.5 wt % to about 8 wt %, about 1 wt % to about 5 wt %, about 1 wt % to about 4 wt %, or about 1 wt % to about 3 wt % of an agent for adjusting the osmolarity of the solution, emulsion, or suspension. In some embodiments, the solution, emulsion, or suspension of the disclosure has an osmolarity from about 10 mOsm to about 1000 mOsm, about 100 mOsm to about 700 mOsm, about 200 mOsm to about 400 mOsm, about 250 mOsm to about 350 mOsm or about 290 mOsm to about 310 mOsm.

In some embodiments, solutions, emulsions, or suspensions of the present disclosure further comprise a buffering agent, such as tromethamine, potassium phosphate, sodium phosphate, saline sodium citrate buffer (SSC), acetate, saline, physiological saline, phosphate buffer saline (PBS), 4-2-hydroxyethyl-1-piperazineethanesulfonic acid buffer (HEPES), 3-(N-morpholino)propanesulfonic acid buffer (MOPS), and piperazine-N,N'-bis(2-ethanesulfonic acid) buffer (PIPES), sodium acetate-boric acid stock solution, boric acid-sodium carbonate with sodium chloride solution, boric acid-sodium borate buffer, sodium and potassium phosphate buffers, boric acid-sodium carbonate with potassium chloride, or combinations thereof. In some embodiments, the solution, emulsion, or suspension comprises from about 0.05 wt % to about 5 wt %, about 0.1 wt % to about 4 wt %, about 0.1 wt % to about 3 wt %, about 0.1 wt % to about 2 wt %, or about 0.1 wt % to about 1 wt % of an agent for buffering the solution, emulsion, or suspension.

In some embodiments, the solution emulsion or suspension provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and combinations thereof.

Salts

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The compounds may be synthesized using conventional techniques. Advantageously, these compounds are conveniently synthesized from readily available starting materials. Synthetic chemistry transformations and methodologies useful in synthesizing the compounds described herein are known in the art.

The present disclosure provides salts of any one or both of an ophthalmic agent and a preservative. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is an ammonium salt, a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the present disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, imidazole, or pyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, an imidazole salt, or a pyrazine salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucuronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

The methods and formulations described herein include the use of amorphous forms as well as crystalline forms (also known as polymorphs). Active metabolites of compounds or salts of any one of the compounds of the present disclosure having the same type of activity are included in the scope of the present disclosure. In addition, the compounds described herein can exist in unsolvated as well as solvated forms with pharmaceutically acceptable solvents such as water, ethanol, and the like. The solvated forms of the compounds and salts presented herein are also considered to be disclosed herein.

In some embodiments, an aqueous solutions, emulsions, or suspensions of the disclosure comprises at least 90 wt % water, such as at least 91 wt %, at least 92 wt %, at least 93 wt %, at least 94 wt %, at least 95 wt %, at least 96 wt %, at least 97 wt %, at least 98 wt %, or even at least 99 wt % of water.

Preservative Removal Agent

The present disclosure provides a preservative removal agent (e.g. a matrix). A preservative removal agent may rapidly and selectively remove preservatives of the present disclosure from a solution, emulsion, or suspension comprising an ophthalmic agent. The preservative removal agent may rapidly and selectively extract the preservative, allowing the eye drop formulation to flow through the plug with minimal pressure drop, yet with sufficient time to remove the preservative and with sufficient surface area and chemistry to adsorb the preservative. The matrix may comprise a material with a high affinity for the preservative, such as for example benzalkonium chloride (BAK), and at the same time a low affinity for a drug or other ophthalmological agent especially in this invention when the drug is also in the complex with a complexing of capping agent. The preservative removal agent may be sufficiently selective, such that at least 50 percent of the preservative may be removed and at least 50 percent of the drug may be retained by the solution. BAK (benzalkonium chloride) can also go under a number of synonyms: alkylbenzyldimethylammonium chloride, alkyldimethylbenzylammonium chloride, benzyl ammonium chloride to name a few. It is also defined by a structure such as Formula: $C_6H_5CH_2N(CH_3)_2RCl$ ($R=C_8H_{17}$ to $C_{18}H_{37}$) with a CAS Number: 63449-41-2. For most purposes in ophthalmic applications and formulations PharmaGrade, EP, USP, JP, manufactured under appropriate GMP controls for pharma or biopharmaceutical production is used.

Non-limiting examples of a preservative removal agents may comprise solid, gel, and/or particulate matrices. The preservative removal agent may act as a physical barrier or filter. Additionally, or alternatively, the preservative removal agent may chemically remove a preservative such as by adsorption of the preservative onto the matrix. The preservative removal agent may be disposed in the outlet of a container, which container may contain the solution, emulsion, or suspension.

In some embodiments, the preservative removal agent comprises an active polymeric matrix component and an inactive polymeric matrix component. In some embodiments, the inactive polymeric matrix component is a polyolefin in the form of a ground powder or a spherical bead. In some embodiments, the shape of the polyolefin particle is regular. In some embodiments, the shape of the polyolefin particle is irregular. In some embodiments, the polyolefin particle size is from about 1 micron to about 1000 microns. In some embodiments, the polyolefin particle size is from about 10 microns to about 700 microns. In some embodiments, the polyolefin particle size is from about 50 microns to about 600 microns.

In some embodiments, the inactive polymeric matrix component is an inert material selected from metal or glass, wherein the inert material is in bead or powder form. In some embodiments, the inactive polymeric matrix component is an inert material coated with a surface antimicrobial material which renders the matrix resistant to bacterial or fungal growth during the storage and use.

In some embodiments, the inactive polymeric matrix component is a polyolefin having substantially no affinity for the ophthalmic agent, or combination of agents, being administered. In some embodiments, substantially no affinity means less than 0.1% of the ophthalmic agent(s) is retained. In some embodiments, substantially no affinity means less than 0.5% of the ophthalmic agent(s) is retained. In some embodiments, substantially no affinity means less than 1.0% of the ophthalmic agent(s) is retained. In some embodiments, substantially no affinity means less than 1.5% of the ophthalmic agent(s) is retained. In some embodiments, substantially no affinity means less than 2.0% of the ophthalmic agent(s) is retained. In some embodiments, substantially no affinity means less than 2.5% of the ophthalmic agent(s) is retained. In some embodiments, substantially no affinity means less than 3.0% of the ophthalmic agent(s) is retained. In some embodiments, substantially no affinity means less than 4.0% of the ophthalmic agent(s) is retained. In some embodiments, substantially no affinity means less than 5.0% of the ophthalmic agent(s) is retained.

In some embodiments, the polymeric matrix comprises an active matrix component and an inactive matrix component in a ratio of about 1% (w/w) to about 99% (w/w). In some embodiments, the polymeric matrix comprises an active matrix component and an inactive matrix component in a ratio of at least about 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, or 1:95, and/or a ratio of no more than about 1:1, 1:2, 1:3, 1:4, 1:5, 1:6, 1:7, 1:8, 1:9, 1:10, 1:20, 1:30, 1:40, 1:50, 1:60, 1:70, 1:80, 1:90, or 1:95 (w/w ratio of active matrix component to inactive matrix component). In some embodiments, the polymeric matrix comprises an active matrix component and an inactive matrix component in a ratio of about 10% (w/w) to about 90% (w/w). In some embodiments, the polymeric matrix comprises an active matrix component and an inactive matrix component in a ratio of about 20% (w/w) to about 80% (w/w). In some embodiments, the polymeric matrix comprises an active matrix component and an inactive matrix component in a ratio of about 30% (w/w) to about 70% (w/w). In some embodiments, the polymeric matrix comprises an active matrix component and an inactive matrix component in a ratio of about 50% (w/w).

The manner in which the blend is prepared can be varied. One embodiment provides the preservative-absorbing polymeric matrix comprising an active matrix component and an inactive matrix component, wherein the preservative-absorbing polymeric matrix is prepared by simple dry blend by mixing the two component polymers together at the appropriate ratio. One embodiment provides the preservative-absorbing polymeric matrix comprising an active matrix component and an inactive matrix component, wherein the preservative-absorbing polymeric matrix is prepared by suspending the two matrix components in a liquid, such as water, alcohol or a solvent that does not dissolve the two matrix components, and then mixing the suspension of particles, filtering and drying the solid mixture to create the blended product. One embodiment provides the preservative-absorbing polymeric matrix comprising an active matrix component and an inactive matrix component, wherein the preservative-absorbing polymeric matrix is prepared by adding the inactive matrix component to a mixture of monomers during the polymerization to prepare the active matrix component, followed by filtering and drying the final mixture to provide the blended preservative-absorbing polymeric matrix.

In some embodiments, a matrix disposed within a nozzle may be a porous polymeric matrix. The porous polymeric matrix may comprise a variety of materials. Such material may be safe and biocompatible. Such material may comprise but is not limited to, for example, Poly(2-hydroxyethyl methacrylate) (pHEMA), poly(hydroxylethyl methacrylate-co-methacrylic acid), crosslinked polyacrylamide, dimethyl acrylamide, methyl methacrylate, silicones, and/or any combination of the preceding materials.

In some embodiments, the matrix may be highly porous. The pore size in the matrix may be small enough so that the molecules, which may initially be far from the surface of the polymer in the matrix, may diffuse towards the polymer and adsorb. A matrix may have large interconnected pores which may allow flow of solution and adsorption of the preservative into the pores. The matrix may be formed as a porous gel, as a packed bed, and/or a structure formed by 3D printing soft lithography, electrospinning, or any other appropriate method. In some embodiments, the matrix may comprise a microporous gel. In some embodiments, the matrix may comprise a packed bed of pHEMA or crosslinked polyacrylamide or other polymeric particles. The particles may be macroporous. The particles may be spherical or non-spherical. In some embodiments, the polymeric matrix may comprise nano or micron sized polymeric particles (e.g., nanogels or microgels). In some embodiments, the polymeric matrix may comprise a cryogel. In some embodiments, the polymeric matrix may be termed a hydrogel, be hydrophilic and absorb water readily. In some embodiments, the particles themselves may directly impart the preservative effect, such as colloidal silver nanoparticles.

In certain embodiments, particles of the formulations described herein have an average diameter from about 1 nm to about 10 µm, about 1 nm to about 10 µm, about 1 nm to about 5 µm, about 1 nm to about 2 µm, about 1 nm to about 1 µm, about 1 nm to about 900 nm, about 1 nm to about 800 nm, about 1 nm to about 700, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, greater than 80% of the particles, such as greater than 90% or greater than 95% of the particles in the formulation have an average largest particle diameter of from about 1 nm to about 1000 µm, about 1 nm to about 10 µm, about 1 nm to about 5 µm, about 1 nm to about 2 µm, about 1 nm to about 1 µm, about 1 nm to about 900 nm, about 1 nm to about 800 nm, about 1 nm to about 700, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, particles of the porous polymeric matrix described herein have an average diameter from about 100 nm to about 10 µm, about 100 nm to about 10 µm, about 100 nm to about 5 µm, about 100 nm to about 2 µm, about 100 nm to about 1 µm, about 100 nm to about 900 nm, about 100 nm to about 800 nm, about 100 nm to about 700, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In certain embodiments, greater than 80% of the particles of the porous polymeric matrix, greater than 90% of the particles of the porous polymeric matrix, or greater than 95% of the particles of the porous polymeric matrix have an average diameter from about 100 nm to about 10 µm, about 100 nm to about 10 µm, about 100 nm to about 5 µm, about 100 nm to about 2 µm, about 100 nm to about 1 µm, about 100 nm to about 900 nm, about 100 nm to about 800 nm, about 100 nm to about 700, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In certain embodiments, greater than 80% of the particles of the porous polymeric matrix, greater than 90% of the particles of the porous polymeric matrix, or greater than 95% of the particles in the formulation have an average diameter from about 10 µm to about 100 µm, about 50 µm to about 200 µm, about 90 µm to about 180 µm, about 150 µm to about 250 µm, about 200 µm to about 350 µm about 250 µm to about 500 µm, about 350 µm to about 800 µm, about 500 µm to about 1000 µm In certain embodiments, the average diameter is the average largest diameter or the average equivalent diameter. The particles may be irregular, regular, spherical, ovoid, or generally of any shape and the size can be defined as passing through a certain sized screen sieve.

The matrix may comprise a tortuosity such that the flow path of a solution, emulsion, or suspension through the nozzle may be significantly increased. In an embodiment where the matrix is a packed bed of macroporous particles, the packed beds of macroporous particles may have three levels of porosity: the space between the particles, the macropores in the particles, and the inherent porosity of the polymer. In such an embodiment, all three levels of porosity may contribute to the tortuosity of the matrix.

In some embodiments, a matrix disposed within a nozzle may be a porous polymeric matrix. Applying a pressure behind the nozzle may cause fluid to flow through the nozzle via the flow path, along which path the preservative may be removed by adsorption onto the matrix. The polymer material, the hydraulic permeability, the partition coefficient, the adsorption rate, and the pore size in combination may aid in the absorption of all or most of the preservative from the solution and thus patient eye drops. The reduced preservative solution may subsequently be delivered directly to the eye. The porous polymeric matrix may rapidly and selectively extract the preservative, allowing the eye drop formulation to flow through the plug with minimal pressure drop, yet with sufficient time to remove the preservative and with sufficient surface area to adsorb the preservative. The matrix may comprise a material with a high affinity for the preservative, such as for example benzalkonium chloride (BAK), and low affinity for a drug or other ophthalmological agent. The porous polymeric matrix may comprise a high affinity for the preservative, such that at least 50 percent of the preservative may be removed and at least 50 percent of the drug may be retained by the solution.

The porous polymeric matrix may comprise a variety of materials. Such material are safe and biocompatible. A polymer of the present disclosure may comprise various monomers, for example, Poly(2-hydroxyethyl methacrylate) (pHEMA) and/or acrylamide (AM), dimethyl acrylamide (DMA) and/or methyl methacrylate (MMA) and/or N-Vinylpyrrolidone (NVP) and/or 2-acrylamido-2-methylpropane sulfonic acid (AMPS) and/or polyvinyl alcohol (PVA) and/or polymethylpropane sulfonic acid (PAMPS) and/or 2-sulfoethyl methacrylate (SEM) and/or acrylic acid (AA) and/or vinylphosphonic acid (VP) and/or t-butyl methacrylate (TBM) and/or Methacryloxypropyltris(trimethylsiloxy) silane (TRIS) and/or t-amyl methacrylate and/or n-octyl methacrylate and/or iso-decyl methacrylate and/or n-decyl methacrylate and/or n-dodecyl acrylate and/or n-hexyl acrylate and/or n-dodecyl acrylate and/or N-(n-Octadecyl)acrylamide and/or silicones and/or any combination of the preceding materials. The polymeric matrix may further comprise a cross linker. A crosslinker may comprise N,N'-methylenebis(acrylamide) (MBAM) and/or triacrylamido triazine (TATZ) and/or SR 351 and/or SR9035 and/or any combination of the preceding materials.

In some embodiments, the matrix material is a copolymer. A copolymer may comprise more than one species of monomer. Copolymers may be branched. Copolymers may be linear. Copolymers may comprise crosslinkers. Copolymers may be block copolymers, may be alternating copolymers, may be periodic copolymers, may be gradient copolymers may be statistical copolymers, may be stereoblock copolymers. The copolymers may exhibit phases of differing hydrophobicity or hydrophilicity. The hydrophobicity and/or hydrophilicity of the one or more monomers or cross-linkers may control the binding of a therapeutic agent or a preservative to the plug material.

In some embodiments, the polymeric matrix is polyvinyl alcohol crosslinked with citric acid or other suitable cross-linking agent to render it a hydrophilic hydrogel. In some embodiments, the polymeric matrix is crosslinked polyvinylpyrrolidone, crosslinked polyethylene oxide, crosslinked polyacrylamides, crosslinked copolymers of methacrylic acid, polyacrylic acid and copolymers such as poly (acrylic acid-co-acrylamide), or poly (methacrylic acid-co-acrylamide).

Polymers of the present disclosure may generally follow an A/B/C formula where A and B are monomers, C is one or more cross-linkers, and A and B are not the same monomer. In some examples, A may be an anionic hydrophilic monomer. In an A/B/C formula, monomers of type A may comprise AM or NVP. In some examples, B may be an ionic hydrophilic monomer. In an A/B/C formula, monomers of type B may comprise MAA, AMPS, SEM, AA, or VP. In some examples, C may be a crosslinker. In an A/B/C formula, monomers of type C may comprise one or more of MBAM, TATZ, or SR 351. Polymers of the present disclosure may generally follow an A/C formula where A is a monomer as described above and C is one or more cross-linkers as described above. Polymers of the present disclosure may generally follow an B/C formula where B is a monomer as described above and C is one or more cross-linkers as described above.

Polymers of the present disclosure may also comprise grafted copolymers such that components such as monomer A and with a cross-linker C are first copolymerized to form a crosslinked copolymer that can be isolated as a small bead or other shaped particle. These beads or particles can then be reswollen in water and a monomer of B type can added and then polymerized into or onto the bead or particle through the use a free radical "grafting" polymerization. In this embodiment the particles are made up of A/C copolymer with a "grafted" B polymer as part of the copolymer structure.

The following is a non-exhaustive list of examples of polymers of the present disclosure. The following includes polymer components and percent compositions, separated by slashes, respectively. Polymers of the present disclosure may comprise: AMPS/MBAM/TATZ 7.5/82.5/10, AMPS/MBAM/TATZ 7.5/77.5/15, AMPS/MBAM 7.5/92.5, Bio-Rad Beads/AMPS 1 g/0.5, AMPS/MBAM 7.5/92.5, AMPS/MBAM/TATZ 7.5/87.5/5.0, SEM/MBAM 7.5/92.5, AM/2-Sulfoethyl MA(SEM)/MBAM 30/10/60, AMPS/MBAM 7.5/92.5; AMPS/MBAM 7.5/92.5, AMPS/MBAM 7.5/92.5, AMPS/MBAM 7.5/92.5, PVA/PAMPS/CA 4.8/1.2/2.4 IPN, AMPS/MBAM 7.5/92.5 ISP, NVP/AMPS/MBAM/TATZ 30/10/30/30, AMPS/MBAM 7.5/92.5, N-vinylpyrrolidinone/AMPS/MBAM 30/10/60, AA/SR351 40/60, AA/MBAM/SR351 60/30/10, AM/2-Sulfoethyl MA (SEM)/MBAM 15/25/60, AA/MBAM 40/60, AA/MBAM 50/50, and VP/AA/MBAM 10/45/45.

Any matrix material and any drug in association with a complexing agent may be used such that the drug/complex partition coefficient into the matrix may be lower by at least an order of magnitude or 2 orders of magnitude than the matrix's affinity for the preservative. For example, pHEMA, or $SO_3-$ or $PO_3H-$ or $COO-$ groups on the polymer (or matrix) may bind BAK with a partition coefficient of about 100-500, or in some embodiments, 1000 depending on the BAK concentration and the structure of the matrix and the % content of those groups. In some embodiments, the matrix may comprise a partition coefficient for the preservative from the solution, emulsion, or suspension of, for example, at least 10, at least 100, at least 1000, at least 10,000, or within a range defined by any two of the preceding values. Additionally, or alternatively, the adsorption rate constant may be sufficiently high so that the time for adsorption of a drug molecule to the polymer may be less than the time to form a drop. The time to form a drop may comprise a time within a range from 0.1 to 10 seconds.

The matrix may display a high hydraulic permeability such that relatively little pressure may be required to dispense a fluid. The hydraulic permeability may depend on the design of the filter. Larger pores in the matrix may allow for higher flow for a given pressure drop. In some embodiments, hydraulic permeability may be larger than about 0.01 Darcy. A nozzle may comprise a permeability of about 0.1 Darcy. A hydraulic permeability of 1 to 10 Darcy may allow fluid to be retained in the filter during instances when the pressure may be lowered subsequent to formation of a drop. A larger hydraulic permeability may allow the same plug to work for a wide range of formulations including, for example, high viscosity formulations, such as rewetting eye drops. In some embodiments, the porous polymeric matrix comprises a hydraulic permeability of, for example, 0.01 Da, 0.1 Da, 1 Da, 10 Da, 100 Da, 1000 Da or a hydraulic permeability within a range defined by any two of the preceding values.

In some embodiments, the matrix may be highly porous. The pore size in the matrix may be small enough so that the molecules, which may initially be far from the surface of the polymer in the matrix, may diffuse towards the polymer and adsorb. A matrix may comprise large interconnected pores which may allow flow of solution and adsorption of the preservative into the pores. The matrix may be formed as a porous gel, as a packed bed, and/or a structure formed by 3D printing soft lithography, electrospinning of a fiber, or any other appropriate method. In some embodiments, the matrix may comprise a microporous gel. In some embodiments, the matrix may comprise a packed bed of pHEMA or cross-linked polyacrylamide with an anionic moiety or functionality as part of the polymer or other polymeric particles. The particles may be spherical or non-spherical. In some embodiments, the polymeric matrix may comprise nano or micron sized or 10s of microns or 100s of microns of polymeric particles (e.g., nanogels or microgels). In some embodiments, the polymeric matrix may comprise a cryogel. In some embodiments, the particles themselves may directly impart the preservative effect, such as colloidal silver nanoparticles.

In some embodiments, the particles may need to be stably held in the nozzle and prevented from eluting from the nozzle. The particles may be attached to the container walls through long polymeric chains and/or by placing a filter at the exit from the device. Additionally, or alternatively, the walls of the container or other surfaces may comprise preservative attached thereupon and/or incorporated therein. In such embodiments, the preservative source comprises a pHEMA membrane with 1-10% by volume equilibrated with BAK. In some embodiments, the matrix comprises preloaded with BAK at a concentration to inhibit microbial growth over time.

In some embodiments, the porous matrix material may comprise a tortuosity such that the flow path of a solution, emulsion, or suspension through the nozzle increases. In some embodiments where the matrix comprises a packed bed of macroporous particles, the packed beds of macroporous particles may comprise three levels of porosity: the space between the particles, the macropores in the particles, and the inherent porosity of the polymer. In such embodiments, all three levels of porosity may contribute to the tortuosity of the matrix. The tortuosity of the porous material combined with the geometry nozzle itself may increase the flow path in accordance with a multiplicative factor of a first flow path length corresponding to flow defined by the nozzle geometry and a second flow path length corresponding to the tortuosity of the porous material.

The pressure needed for drop creation may exceed the Young Laplace pressure during drop creation, which may be about $2\sigma/R_d$ where $\sigma$ is the surface tension and $R_d$ is the radius of the drop. Estimating $R_d \sim 0.5$ mm based on a drop volume of 30 µL, and using the surface tension of water may yield a Young Laplace pressure of about 100 Pa. The pressure to form a drop may additionally exceed the pressure needed to displace 30 µL of volume. Typical drop volumes may comprise a volume within a range between 1 µL and 100 µL. The minimum pressure to form a drop may be 0.01 Atm (1000 Pa) based on an ideal gas estimate using a 3 mL bottle at atmospheric pressure, but may be lower for larger bottles at varying pressures. Maximum pressure to form a drop may be limited by a patient strength. The pressure to form a drop may be within a range between 0.01 Atm and 0.5 Atm.

The rate of liquid flow through the plug may depend on the applied pressure as well as the design parameters of the matrix including, but not limited to, length, area, porosity, hydraulic permeability, flow path length, etc. These design parameters may be considered individually or in combination to remove preservative without excessive squeeze pressure. The rate of liquid flow may affect the time to form a drop.

Dosage

The dosage and frequency (single or multiple doses) administered to a mammal may vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents may be used in conjunction with the methods and compounds of this disclosure. Adjustment and manipulation of established dosages (e.g., frequency and duration) are well within the ability of those skilled in the art.

Dosages may be varied depending upon the requirements of the patient and the compound being employed. The dose administered to a patient, in the context of the present disclosure should be sufficient to affect a beneficial therapeutic response in the patient over time. The size of the dose also may be determined by the existence, nature, and extent of any adverse side effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals may be adjusted individually to provide levels of the administered compound effective for the particular clinical indication being treated. This may provide a therapeutic regimen that is commensurate with the severity of the individual's disease state

EXAMPLES

It is understood that the examples and embodiments described herein are for illustrative purposes only and are not intended to limit the scope of the claimed invention. It is also understood that various modifications or changes in light of the examples and embodiments described herein will be suggested to persons skilled in the art and are to be included within the spirit and purview of this application and scope of the appended claims. All publications, patents, and patent application cited herein are hereby incorporated by reference in their entirety for all purposes.

It will be understood that various ophthalmic agents may be used in any aspect of the disclosure provided. Porous polymeric hydrogel A as prepared and used in the examples described herein is done so for demonstration purposes. It will be understood that various porous polymer hydrogel materials may be used in any aspect of the disclosure provided.

Example 1

Preparation of Active Hydrogel a and Active Hydrogel a Blended with LDPE

The materials in the table below were used in the procedure to prepare active hydrogel A.

To a solution of SEM (2-Sulfoethyl Methacrylate) in water was added beads of Bio-Gel P-4 Gel, Medium, and the mixture was heated to 55° C. Then KPS (2 mol %, 40 mg/mL stock solution in water) was added to the slurry of beads and SEM. The temperature was increased to 70° C. for 6 hours. The product was worked-up by centrifuge washing with IPA and water in a 50 mL tube. The solid was collected by filtration and dried in a vacuum oven. The dried solid was sieved, purified with water and then with IPA in a soxhlet extractor, and dried. Finally, the dried product was re-sieved to get particles between 500 and 60 microns.

| Charge Table per 20 mL vial | |
|---|---|
| Cmpd | D-322-034-02 |
| SEM | 0.5 g |
| water | 10 mL (20 vol) |
| Bio-Rad P-4 beads (available from Bio-Rad Corporation) | 1.0 g |
| KPS (potassium persulfate from Sigma-Aldrich | 26.1 mg (0.35 mL) |

Active hydrogel A blended 50/50 wt % was prepared by simple dry blending of the active and inactive polymer powders.

Example 2

Determination of Variation of Drug Concentration

As shown in Table 1, in the comparative example 1, the active hydrogel A is used without any addition of the inactive polyolefin. In the comparative example 2, the same active hydrogel A is blended at a 50/50 ratio. The polymers are placed into dispensing tips with 172 mg in each tip and placed on bottles of ophthalmic solutions of latanoprost containing a bulk concentration (starting concentration in the bottle) of 50 ppm of drug. The formulation was prepared by dissolving latanoprost 50 ppm with HPβCD (8.1 mg/ml) Mw 1396 Sigma Product #C0926) and BAK (100 ppm, Sigma Product #12063) in water. Drops were then expressed one at a time from the bottles through the tips packed with the polymers and then the drug concentration in each drop is measured by HPLC. The average of 5 bottles is taken in each case for the ppm of latanoprost in each drop and then the average % label claim is shown in each drop. As illustrated in Table 1, for the active hydrogel A blended with LDPE, the range of variation and absolute change in concentration is minimal after 5 drops. The results show the concentrations of the 100% active hydrogel drops have a standard deviation of approximately 13.9 ppm (~27.8%), whereas the 50/50 wt. % blend has a standard deviation of approximately 7.1 ppm (~14.1%).

TABLE 1

| | Comparative Example 1 100% Active Hydrogel A Bulk concentration of latanoprost in bottle = 50 ppm | | Comparative Example 2 Blend of 50/50 wt. % LDPE and Active Hydrogel A Bulk concentration of latanoprost in bottle = 50 ppm | |
|---|---|---|---|---|
| Drop number | Drop Concentration (ppm) Avg (n = 5) | % change | Drop Concentration (ppm) Avg (n = 5) | % change |
| 1 | 91 | 182% | 63 | 126% |
| 2 | 83 | 165% | 69 | 138% |
| 3 | 68 | 136% | 56 | 112% |
| 4 | 63 | 126% | 53 | 106% |
| 5 | 57 | 114% | 46 | 93% |
| 6 | 55 | 110% | 50 | 100% |
| 7 | 53 | 106% | 51 | 101% |
| 8 | 54 | 107% | 50 | 100% |
| 9 | 51 | 103% | 51 | 101% |
| 10 | 53 | 106% | 49 | 98% |
| Average | 63 | 125% | 54 | 108% |

As shown in Table 2, in the comparative example 3, the active hydrogel B is used without any addition of the inactive polyolefin. Active hydrogel B is an oxidized polyethylene available from Honeywell A-C 395A; sieved fraction at 63-125 um). In the comparative example 4, the same active hydrogel B is blended at a 50/50 ratio with LDPE powder. The polymers are placed into dispensing tips with 172 mg in each tip and placed on bottles of ophthalmic solutions of brimonidine tartrate containing a bulk concentration (starting concentration in the bottle) of 2.0 mg/mL of brimonidine tartrate. Drops were then expressed one at a time from the bottles through the tips packed with the polymers and the brimonidine tartrate concentration in each drop is measured by HPLC. The average of 5 bottles is taken in each case for the ppm of drug in each drop and then the average % label claim is shown in each drop. As illustrated in Table 2, for the active hydrogel B blended with LDPE, the range of variation and absolute change in concentration is minimal from the first drop. The results show the concentrations of the 100% active hydrogel drops have a standard deviation of approximately 0.052 mg/mL (~5.2%), whereas the 50/50 wt. % blend has a standard deviation of approximately 1.2 mg/mL (~1.2%).

TABLE 2

| | Comparative Example 3 100% Active Hydrogel B Bulk concentration of brimonidine tartrate in bottle = 2.0 mg/mL | | Comparative Example 4 Blend of 50/50 wt. % LDPE and Active Hydrogel B Bulk concentration of brimonidine tartrate in bottle = 2.0 mg/mL | |
|---|---|---|---|---|
| Drop number | Drop Concentration (mg/mL) Avg (n = 5) | % change | Drop Concentration (mg/mL) Avg (n = 5) | % change |
| 1 | 1.96 | 96% | 1.98 | 98% |
| 2 | 1.89 | 89% | 1.96 | 96% |
| 3 | 1.79 | 79% | 1.95 | 95% |
| 4 | 1.83 | 83% | 1.95 | 95% |
| 5 | 1.84 | 84% | 1.96 | 96% |
| 6 | 1.88 | 88% | 1.96 | 96% |
| 7 | 1.85 | 85% | 1.97 | 97% |
| 8 | 1.90 | 90% | 1.98 | 98% |
| Average | 1.87 | 87% | 1.96 | 96% |

The procedure for demonstrating the selective absorption of the BAK preservative from a drug solution was described previously in U.S. Pat. No. 10,123,904, which is incorporated herein by reference in its entirety.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A preservative removing device, comprising:
 a polymeric matrix, wherein the polymeric matrix is configured to selectively absorb a preservative when a solution, emulsion, or suspension comprising an ophthalmic agent and a preservative is passed therethrough, and wherein the polymeric matrix comprises an active matrix component and an inactive matrix component.

2. The device of claim 1, wherein the inactive matrix component has substantially no affinity for the ophthalmic agent or the preservative.

3. The device of claim 1, wherein the active matrix component is a polymeric hydrogel.

4. The device of claim 1, wherein the inactive matrix component is a polyolefin.

5. The device of claim 4, wherein the polyolefin is a polyethylene, polypropylene, or a copolymer thereof.

6. The device of claim 4, wherein the polyolefin is a low-density polyethylene (LDPE).

7. The device of claim 1, wherein the solution, emulsion, or suspension comprising an ophthalmic agent and a preservative is contained in a container suitable for drop-wise dispensing.

8. The device of claim 1, wherein the ophthalmic agent comprises latanoprost.

9. The device of claim 1, wherein the ophthalmic agent comprises timolol and brimonidine.

10. The device of claim 1, wherein the ophthalmic agent comprises brimonidine.

11. The device of claim 1, wherein the preservative is an ionic preservative.

12. The device of claim 1, wherein the polymeric matrix is a hydrogel and the preservative is benzalkonium chloride.

13. The device of claim 1, wherein the polymeric matrix comprises 2-hydroxyethylmethacrylate, tert-butyl methacrylate, or a combination thereof.

14. The device of claim 1, wherein the polymeric matrix comprises a crosslinker.

15. The device of claim 14, wherein the crosslinker is SR-9035.

16. The device of claim 1, wherein the solution, emulsion, or suspension is disposed within a chamber of a compressible bottle, and the polymeric matrix is disposed between the chamber and an outlet of the compressible bottle.

17. The device of claim 16, wherein compression of the compressible bottle passes the solution, emulsion, or suspension through the polymeric matrix to the outlet.

18. The device of claim 1, wherein the concentration of the ophthalmic agent after passing though the polymeric matrix is at least 95% of the concentration of the ophthalmic agent before passing through the polymeric matrix.

19. The device of claim 1, wherein the concentration of the preservative after passing though the polymeric matrix is less than 10% of the concentration of the preservative before passing through the polymeric matrix.

20. The device of claim 1, wherein the polymeric matrix is a hydrogel formed from a polyvinyl alcohol crosslinked with a crosslinking agent.

21. The device of claim 1, wherein the polymeric matrix is selected from crosslinked polyvinylpyrrolidone, crosslinked polyethylene oxide, crosslinked polyacrylamides, crosslinked copolymers of methacrylic acid, polyacrylic acid, or copolymers selected from poly (acrylic acid-co-acrylamide), or poly (methacrylic acid-co-acrylamide).

22. The device of claim 1, wherein the polymeric matrix is hydrogel prepared from polyacrylamide crosslinked with at least one crosslinking monomer selected from N,N'-methylenebis(acrylamide) (MBAM), triacrylamido triazine (TATZ), SR 351, or SR9035; and the crosslinked polyacrylamide is modified with at least one modifying monomer selected from methyl methacrylate (MAA), 2-acrylamido-2-methylpropane sulfonic acid (AMPS), 2-sulfoethyl methacrylate (SEM), acrylic acid (AA), or vinylphosphonic acid (VP).

23. The device of claim 1, wherein the polymeric matrix is hydrogel prepared from polyacrylamide crosslinked with N,N'-methylenebis(acrylamide) (MBAM); and the crosslinked polyacrylamide is modified with 2-sulfoethyl methacrylate (SEM).

24. The device of claim 1, wherein the polymeric matrix is hydrogel prepared from polyacrylamide crosslinked with at least one crosslinking monomer selected from N,N'-methylenebis(acrylamide) (MBAM), triacrylamido triazine (TATZ), SR 351, or SR9035; the crosslinked polyacrylamide material is isolated; and the crosslinked polyacrylamide material is modified with at least one modifying monomer selected from methyl methacrylate (MAA), 2-acrylamido-2-methylpropane sulfonic acid (AMPS), 2-sulfoethyl methacrylate (SEM), acrylic acid (AA), or vinylphosphonic acid (VP).

25. The device of claim 1, wherein the polymeric matrix is hydrogel prepared from polyacrylamide crosslinked with N,N'-methylenebis(acrylamide) (MBAM; the crosslinked polyacrylamide material is isolated; and the crosslinked polyacrylamide material is modified with at least one modifying monomer selected from 2-acrylamido-2-methylpropane sulfonic acid (AMPS), or 2-sulfoethyl methacrylate (SEM).

\* \* \* \* \*